(12) United States Patent
Handlon

(10) Patent No.: US 6,465,451 B1
(45) Date of Patent: Oct. 15, 2002

(54) HYPOLIPIDEMIC BENZOTHIAZEPINE COMPOUNDS

(75) Inventor: Anthony Louis Handlon, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/582,907

(22) PCT Filed: Jan. 7, 1999

(86) PCT No.: PCT/EP99/00021

§ 371 (c)(1),
(2), (4) Date: Jul. 6, 2000

(87) PCT Pub. No.: WO99/35135

PCT Pub. Date: Jul. 15, 1999

(30) Foreign Application Priority Data

Jan. 10, 1998 (GB) ................................ 9800428

(51) Int. Cl.$^7$ .......................... A61K 31/55; A61P 9/00; C07D 281/02
(52) U.S. Cl. .................. 514/211.09; 540/552
(58) Field of Search ...................... 540/552; 514/211.09

(56) References Cited

U.S. PATENT DOCUMENTS

| | | | | |
|---|---|---|---|---|
| 5,817,653 A | * | 10/1998 | Elliott et al. ................. | 514/213 |
| 5,910,494 A | | 6/1999 | Brieaddy ..................... | 514/211 |
| 5,998,400 A | * | 12/1999 | Brieaddy et al. ........... | 514/211 |

FOREIGN PATENT DOCUMENTS

| | | |
|---|---|---|
| WO | 95/04534 | 2/1995 |
| WO | WO 9605188 | 2/1996 |
| WO | WO96 16051 A | 5/1996 |

* cited by examiner

*Primary Examiner*—Brenda Coleman
(74) *Attorney, Agent, or Firm*—Lorie Ann Morgan

(57) ABSTRACT

The invention is concerned with novel hypolipidemic compounds of formula (I),

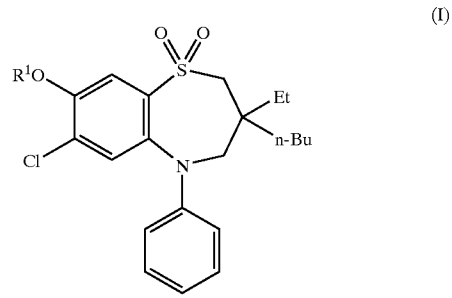

wherein $R^1$ is H or methyl, and salts, solvates or physiologically functional derivatives thereof, with processes and novel intermediates for their preparation, pharmaceutical compositions containing them and with their use in medicine, particularly in the prophylaxis and treatment of hyperlipidemic conditions and associated diseases, such as atherosclerosis.

13 Claims, No Drawings

HYPOLIPIDEMIC BENZOTHIAZEPINE COMPOUNDS

This application is a Rule 371 Application of PCT/EP99/00021, filed Jan. 7, 1999.

The present invention is concerned with new hypolipidemic compounds, with processes and novel intermediates for their preparation, with pharmaceutical compositions containing them and with their use in medicine, particularly in the prophylaxis and treatment of hyperlipidemic conditions and associated conditions such as atherosclerosis.

Hyperlipidemic conditions are often associated with elevated plasma concentrations of low density lipoprotein (LDL) cholesterol. Such concentrations can be reduced by decreasing the absorption of bile acids from the intestine. One method by which this may be achieved is to inhibit the bile acid active uptake system in the terminal ileum. Such inhibition stimulates the conversion of cholesterol to bile acid by the liver and the resulting increase in demand for cholesterol produces a corresponding increase in the rate of clearance of LDL cholesterol from the blood plasma or serum.

The compounds of the present invention reduce the plasma or serum concentrations of LDL cholesterol and in consequence are particularly useful as hypolipidemic agents. By decreasing the concentrations of cholesterol and cholesterol ester in the plasma, the compounds of the present invention retard the build-up of atherosclerotic lesions and reduce the incidence of coronary heart disease-related events. The latter are defined as cardiac events associated with increased concentrations of cholesterol and cholesterol ester in the plasma or serum.

International Patent Application No. PCT/GB/9300328 describes 1,4-benzothiazepine compounds which have hypolipidemic activity. International Patent Application No. PCT/GB95/02700 (published as WO/9616051) describes 1,5-benzothiazepine compounds which also have hypolipidemic activity. A group of substituted 1,5-benzothiazepine compounds has been discovered which have surprising hypolipidemic activity over those specifically disclosed in the prior art.

Accordingly, the present invention provides a compound of formula (I)

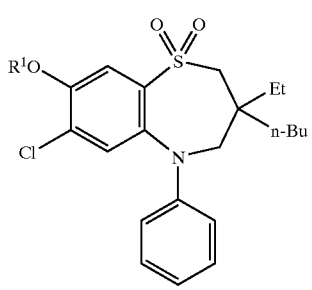

(I)

wherein
$R^1$ is H or methyl; or a salt, solvate or physiologically functional derivative thereof.
Preferably $R^1$ is hydrogen.
Suitable compounds of formula (I) are selected from:
(±)-2,3,4,5-Tetrahydro-3-ethyl-3-butyl-5-phenyl-7-chloro-8-hydroxy-1,5-benzothiazepine-1,1-dioxide;
(3S)-2,3,4,5-Tetrahydro-3-ethyl-3-butyl-5-phenyl-7-chloro-8-hydroxy-1,5-benzothiazepine-1,1-dioxide; and
(±)-2,3,4,5-Tetrahydro-3-ethyl-3-butyl-5-phenyl-7-chloro-8-methoxy-1,5-benzothiazepine-1,1-dioxide; or a salt, solvate or physiologically functional derivative thereof.

Pharmaceutically acceptable salts are particularly suitable for medical applications because of their greater aqueous solubility relative to the parent, i.e., basic, compounds. Such salts must clearly have a pharmaceutically acceptable anion or cation. Suitable pharmaceutically acceptable acid addition salts of the compounds of the present invention include those derived from inorganic acids, such as hydrochloric, hydrobromic, phosphoric, metaphosphoric, nitric, sulphonic and sulphuric acids, and organic acids, such as acetic, benzenesulphonic, benzoic, citric, ethanesulphonic, fumaric, gluconic, glycollic, isothionic, lactic, lactobionic, maleic, malic, methanesulphonic, succinic, p-toluenesulphonic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are within the scope of the invention as useful intermediates for the preparation or purification of pharmaceutically acceptable salts and/or for use in non-therapeutic, for example, in vitro, applications.

Any references to "compound(s) of formula (I)", "compounds of the present invention", "compounds according to the invention" etc., refer to compound(s) of formula (I) as described above or their salts, solvates or physiologically functional derivatives as defined herein.

The term "physiologically functional derivative" as used herein refers to any physiologically acceptable derivative of a compound of the present invention, for example, an ester, which upon administration to a mammal, such as a human, is capable of providing (directly or indirectly) such a compound or an active metabolite thereof. Such derivatives are clear to those skilled in the art, without undue experimentation, and with reference to the teaching of Burger's Medicinal Chemistry And Drug Discovery, 5th Edition, Vol 1: Principles And Practice.

Physiologically functional derivatives, which upon administration to a mammal, such as a human, is capable of providing (directly or indirectly) a compound of the invention or an active metabolite thereof, are commonly referred to as prodrugs. These prodrugs may or may not be active in their own right. Suitably, prodrugs of the present invention are formed at position $R^1$ to give $C_{1-6}$ ester or $C_{1-6}$ alkoxy groups.

Active metabolites are those which may be generated in vivo by the metabolism of the compounds of the present invention and include, for example, glucuronides.

The compounds of the present invention can also exist in different polymorphic forms, for example, amorphous and crystalline polymorphic forms. All polymorphic forms of the compounds of the present invention are within the scope of the invention and are a further aspect thereof.

The compounds of formula (I) are in forms wherein the carbon center —C(Et)(n-Bu)— is chiral. The present invention includes within its scope each possible optical isomer substantially free, i.e. as associated with less than 5%, of any other optical isomer(s), and mixtures of one or more optical isomers in any proportions, including racemic mixtures. The (S)-isomer is preferred.

According to further aspects of the invention, there are also provided:

(a) the compounds of formula (I) and pharmaceutically acceptable salts, solvates and physiologically functional derivatives thereof for use as therapeutic agents, particularly in the prophylaxis and treatment of clinical conditions for which a bile acid uptake inhibitor is indicated, for example, a hyperlipidemic condition, and associated diseases such as atherosclerosis;

(b) pharmaceutical compositions comprising a compound of formula (I) or one of its pharmaceutically acceptable salts, solvates, or physiologically functional derivatives, at least one pharmaceutically acceptable carrier and, optionally, one or more other physiologically active agents;

(c) the use of a compound of formula (I) or of a pharmaceutically acceptable salt, solvate, or physiologically functional derivative thereof in the manufacture of a medicament for the prophylaxis or treatment of a clinical condition for which a bile acid uptake inhibitor is indicated, for example, a hyperlipidemic condition, and associated diseases such as atherosclerosis;

(d) a method of inhibiting the absorption of bile acids from the intestine of a mammal, such as a human, which comprises administering an effective bile acid absorption inhibiting amount of a compound of formula (I) or of a pharmaceutically acceptable salt, solvate, or physiologically functional derivative thereof to the mammal;

(e) a method of reducing the blood plasma or serum concentrations of LDL cholesterol in a mammal, such as a human, which comprises administering an effective cholesterol reducing amount of a compound of formula (I) or of a pharmaceutically acceptable salt, solvate, or physiologically functional derivative thereof to the mammal;

(f) a method of reducing the concentrations of cholesterol and cholesterol ester in the blood plasma or serum of a mammal, such as a human, which comprises administering an effective cholesterol and cholesterol ester reducing amount of a compound of formula (I) or of a pharmaceutically acceptable salt, solvate, or physiologically functional derivative thereof to the mammal;

(g) a method of increasing the fecal excretion of bile acids in a mammal, such as a human, which comprises administering an effective bile acid fecal excretion increasing amount of a compound of formula (I) or of a pharmaceutically acceptable salt, solvate, or physiologically functional derivative thereof to the mammal;

(h) a method for the prophylaxis or treatment of a clinical condition in a mammal, such as a human, for which a bile acid uptake inhibitor is indicated, for example, a hyperlipidemic condition, and associated diseases such as atherosclerosis, which comprises administering a therapeutically effective amount of a compound of the formula (I) or of a pharmaceutically acceptable salt, solvate, or physiologically functional derivative thereof to the mammal;

(i) a method of reducing the incidence of coronary heart disease-related events in a mammal, such as a human, which comprises administering an effective coronary heart disease-related events reducing amount of a compound of formula (I) or of a pharmaceutically acceptable salt, solvate, or physiologically functional derivative thereof;

(j) a method of reducing the concentration of cholesterol in the blood plasma or serum of a mammal, such as a human, which comprises administering an effective cholesterol reducing amount of a compound of formula (I);

(k) processes for the preparation of compounds of formula (I) (including salts, solvates and physiologically functional derivatives thereof as defined herein); and (l) novel chemical intermediates in the preparation of compounds of formula (I).

The compounds of the present invention may be administered conjunctively with other physiologically active agents, including hypolipidemic agents such as bile acid sequestering agents, fibric acid derivatives, or HMG-CoA reductase inhibitors (competitive inhibitors of 3-hydroxy-3-methylglutaryl-coenzyme A reductase), for example statins, such as pravastatin, lovastatin, fluvastatin, or simvastatin.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is in the range of from 0.001 mg to 100 mg (typically from 0.01 mg to 50 mg) per day per kilogram bodyweight, for example, 0.01–10 mg/kg/day. Thus, orally administrable unit dose formulations, such as tablets or capsules, may contain, for example, from 0.1 to 100 mg, typically from 0.1 to 10 mg, preferably 0.1 to 5 mg. In the case of pharmaceutically acceptable salts, the weights indicated above refer to the weight of the benzothiazepine ion derived from the salt.

For the prophylaxis or treatment of the conditions referred to above, the compounds of formula (I) can be used as the compound per se, but are preferably presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present including other compounds of formula (I). The pharmaceutical compositions of the invention can be prepared by any of the well known techniques of pharmacy consisting essentially of admixing the components.

When the compound of formula (I) is used in combination with one or more other physiologically active agents as described hereinbefore, the amount of the other physiologically active agents required to achieve the desired biological effect will also depend on a number of factors. The specific dose and dosing schedule will be readily determinable by those skilled in the art. In general, the dose utilized will be the dose approved for medical use in humans.

Pharmaceutical compositions according to the present invention include those suitable for oral, rectal, topical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used. Enteric-coated and enteric-coated controlled release formulations are also within the scope of the invention. Suitable enteric coatings include cellulose acetate phthalate, polyvinylacetate phthalate, hydroxypropylmethylcellulose phthalate and anionic polymers of methacrylic acid and methacrylic acid methyl ester. Suitable enteric coated and enteric coated controlled release formulations include tablets and capsules.

Pharmaceutical compositions suitable for oral administration can be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or moulding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Moulded tablets can be made by moulding, in a suitable machine, the powdered compound moistened with an inert liquid diluent. Controlled release tablets can be prepared in similar manner and with the addition of, for example, hydroxypropylmethyl cellulose.

Enteric-coated tablets can be prepared by coating the tablets with an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Enteric-coated controlled release tablets can be prepared by coating controlled release tablets with an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Capsules can be prepared by admixing a compound of formula (I) with, for example, magnesium stearate, pregelantinised starch, sodium starch glycollate, and/or magnesium stearate and filling two-part hard gelatin capsules with the resulting mixture.

Controlled release capsule compositions can be prepared by admixing a compound of formula (I) with, for example, microcrystalline cellulose and/or lactose, extruding using an extruder, then spheronising and drying the extrudate. The dried pellets are coated with a release controlling membrane, for example ethyl cellulose, and filled into two-part, hard gelatin capsules.

Enteric capsule compositions can be prepared by admixing a compound of formula (I) with, for example, microcrystalline cellulose and/or lactose, extruding using an extruder, then spheronising and drying the extrudate. The dried pellets are coated with an enteric membrane, for example cellulose acetate phthalate containing a plasticizer, for example diethyl phthalate and filled into two-part, hard gelatin capsules.

Pharmaceutical compositions suitable for buccal (sublingual) administration include lozenges comprising a compound of formula (I) in a flavored base, usually sucrose and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of formula (I), preferably isotonic with the blood of the intended recipient. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of the active compound.

Pharmaceutical compositions suitable for rectal administration are preferably presented as unit-dose suppositories. These can be prepared by admixing a compound of formula (I) with one or more conventional solid carriers, for example, cocoa butter, and then shaping the resulting mixture.

Transdermal administration is also possible. Pharmaceutical compositions suitable for transdermal administration can be presented as discrete patches adapted to remain in intimate contact with the epidermis of the recipient for a prolonged period of time. Such patches suitably contain the active compound in an optionally buffered, aqueous solution, dissolved and/or dispersed in an adhesive, or dispersed in a polymer. A suitable concentration of the active compound is about 1% to 35%, preferably about 3% to 15%. As one particular possibility, the active compound can be delivered from the patch by electrotransport or iontophoresis, for example, as described in Pharmaceutical Research, 3(6), 318 (1986).

The compounds of formula (I) can be prepared by conventional methods known to a skilled person or in an analogous manner to processes described in the art. For example, compounds of formula (I) wherein $R^1$ is H can be prepared from compounds of formula (II)

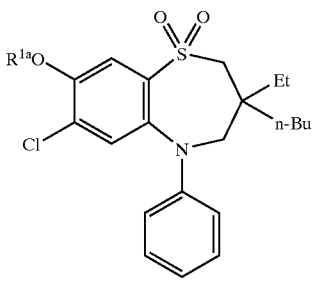

(II)

wherein $R^{1a}$ is an alkyl moiety (e.g., $C_{1-4}$ alkyl, suitably methyl), by dealkylation with a suitable agent, such as boron tribromide, in a suitable organic solvent, for example methylene chloride.

According to a second process (B), a compound of formula (I) wherein $R^1$ is methyl, or a salt, solvate, or physiologically functional derivative thereof, may be prepared from a compound of formula (III)

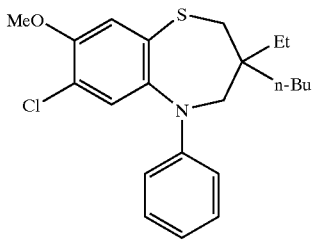

(III)

by oxidation of the sulfur group with, for example, a mixture of osmium tetroxide and N-methyl-morpholine-N-oxide.

Compounds of formula (II) or (III) may be prepared from compounds of formula (IV), wherein $R^{1a}$ is defined above, by methods known in the art, particularly those described in WO96/16051.

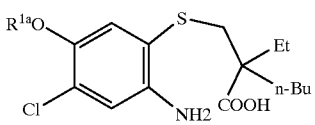

(IV)

Compounds of formula (IV) can be prepared by methods described in WO96/16051 or by reacting compounds of formula (V) with compounds of formula (Va)

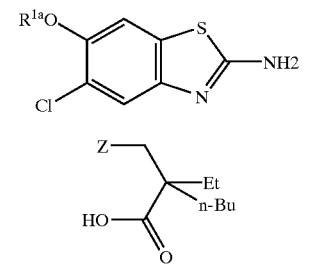

(V)

(Va)

wherein Z is a suitable leaving group, for example, halo, by first reacting the compound of formula (V) with a base, for example aqueous potassium hydroxide at an elevated temperature, for example 100° C., cooling, and then adding the compound of formula (Va).

Compounds of formula (V) can be prepared from compounds of formula (VI)

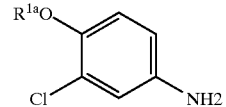

(VI)

by reaction with ammonium thiocyanate and bromine in a suitable solvent such as acetic acid.

Compounds of formula (VI) are commercially available or can be prepared by methods well known or readily available to those skilled in the art.

Compounds of formula (Va) can be prepared from compounds of formula (VII)

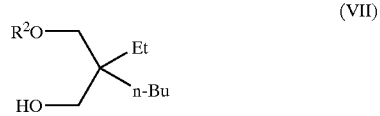

(VII)

wherein $R^2$ is a suitable hydroxy protecting group, for example, tert-butyldimethylsilyl, by oxidation of the compound of formula (VII) with, for example, sodium periodate and ruthenium trichloride in a suitable solvent such as carbon tetrachloride/acetonitrile/water. Subsequent to the oxidation, the $R^2$ protected hydroxy is deprotected and converted to the appropriate leaving group Z by known methods, for example, with HBr.

Compounds of formula (VII) can be prepared from the corresponding diols by methods well known or readily available to those skilled in the art. The diols are commercially available or can be prepared by methods well known or readily available to those skilled in the art.

The compounds of formula (I), substantially free of other optical isomers can be obtained either by chiral synthesis, for example, by the use of the appropriate chiral starting material(s), such as a chiral compound of formula (Va), or by resolution of the products obtained from achiral syntheses, for example, by chiral hplc, enzymatic resolution, or by classical resolution with chiral acids.

Optional conversion of a compound of formula (I), or a compound of formula (I) comprising a basic substituent, to a corresponding acid addition salt may be effected by reaction with a solution of the appropriate acid, for example, one of those recited earlier. Optional conversion of a compound of formula (I) comprising an acidic substituent to a corresponding base salt may be effected by reaction with a solution of the appropriate base, for example, sodium hydroxide. Optional conversion to a physiologically functional derivative, such as an ester, can be carried out by methods known to those skilled in the art or obtainable from the chemical literature.

In addition, compounds of the formula (I) may be converted to different compounds of the formula (I) by standard methods known or available from the literature to those skilled in the art, for example by methylation of a hydroxy group.

For a better understanding of the invention, the following Examples are given by way of illustration and are not to be construed in any way as limiting the scope of the invention.

General Procedures: Proton magnetic resonance spectra were recorded at 300 MHz. Mass spectra were recorded under atmospheric pressure chemical ionization (APCI) conditions on a LCMS instrument or were performed by Oneida Research Services, Inc. under chemical ionization (CI) conditions using methane as the reagent gas. Elemental Analysis were performed by Atlantic Microlab, Inc. All reactions were performed under nitrogen atmosphere. TLC plates were Whatman MK6F silica gel 60 plates and were visualized under a UV lamp. Column chromatography was performed with EM Science silica Gel 60 (230–400 mesh). Reagents were obtained from Aldrich Chemical Co. unless otherwise noted and were used without further purification. Solvents were Aldrich anhydrous grade.

EXAMPLE 1

Preparation of (3S)-2,3,4,5-Tetrahydro-3-ethyl-3-butyl-5-phenyl-7-chloro-8-methoxy-1,5-benzothiazepine-1,1-dioxide and (3S)-2,3,4,5-Tetrahydro-3-ethyl-3-butyl-5-phenyl-7-chloro-8-hydroxy-1,5-benzothiazepine-1,1-dioxide (±)-2-((Tert-butyldimethylsilyl)oxy)methyl-ethyl-hexanol (1). To a slurry of 60% NaH (21.2 g) in 800 ml THF was added in 3 portions 2-n-butyl-2-ethyl-1,3-propanediol (85.0 g) and stirred for 1 h. The mixture was cooled to 0° C. To the resulting gum was added a 1 M solution of tert-butyldimethylsilyl chloride in THF (530 ml) and stirred overnight allowing the solution to warm to RT. The solvent was evaporated and the residue was partitioned between water (400 ml) and ether (300 ml). The ether layer was washed with bicarbonate solution and brine and concentrated. Column chromatography (5% ethyl acetate/petroleum ether) gave 1 as a colorless oil (142.6 g).

MS Da/e=275 (MH$^+$).

Calcd for $C_{15}H_{34}O_2Si$: C, 65.63; H, 12.48. Found: C, 65.87; H, 12.47.

(±)-2-(Bromomethyl)-2-ethyl-hexanoic acid (2). To a solution of 1 (142.6 g) in 300 ml $CCl_4$, 300 ml $CH_3CN$, and 450 ml $H_2O$ at 0° C. was added $NaIO_4$ (283 g) and $RuCl_3$ (2.0 g) and stirred for 20 h allowing the reaction mixture to warm to RT. The reaction mixture was filtered through Celite and the filtrate was concentrated by rotary evaporation. The residue was transferred to a separatory funnel and partitioned between $H_2O$ and $CH_2Cl_2$. The aqueous phase was extracted 3 times with $CH_2Cl_2$, dried, concentrated. The residue was taken up in 48% HBr (500 ml) and refluxed for 24 h. After cooling to RT the solution was transferred to a separatory funnel, extracted 3 times with ethyl ether, washed once with brine, dried over $Na_2SO_4$, and concentrated. The product was purified by column chromatography on silica gel eluting the product with 20% ethyl acetate/petroleum ether giving 2 (111 g).

MS Da/e=157 (M−Br), 237, 239 (M+1).

Calcd for $C_9H_{17}O_2Br$: C, 45.59; H, 7.23; Br, 33.70. Found: C, 46.27; H, 7.17; Br, 32.94.

2-Amino-5-chloro-6-methoxybenzothiazole (4). To a solution of 3-chloro-p-anisidine (3, 58.4 g) in acetic acid (400 ml) was added ammonium thiocyanate and the mixture was stirred for 30 min at RT. The reaction mixture was cooled to 15° C. in an ice bath. To the cooled reaction mixture was added a solution of bromine (17.2 ml) in acetic acid (200 ml) over 10 min. After 10 min stirring the reaction mixture was allowed to warm to RT. After stirring at RT for 3.5 h, the reaction mixture was filtered and the solids caught on filter paper. The solids were transferred to a flask and 200 ml water was added. The suspension was stirred vigorously and 30 ml 50% aqueous NaOH was added. The mixture was filtered catching the product on filter paper. The powder was vacuum oven dried at 120° C. giving 4 (51.0 g)

MS Da/e=215 (M+1).

Calcd for $C_8H_7N_2SOCl$: C, 44.72; H, 3.29; N, 13.05; S, 14.93. Found: C, 44.63; H, 3.30; N, 12.96; S, 14.83.

(±)-2-(((2-Amino-4-chloro-5-methoxy-phenyl)thio)methyl)-2-ethylhexanoic acid (5). To a suspension of 4 (20.0 g) in $H_2O$ (200 ml) was added KOH (100 g). The slurry was refluxed for 7 h and allowed to cool to RT. To the dark solution was added 2 (33.2 g) in one portion. The reaction mixture was stirred for 18 h at which point the pH was adjusted to 4 with HCl. The mixture was transferred to a separatory funnel and extracted three times with ethyl acetate. The organic layer was dried and concentrated. The product was purified by column chromatography on silica gel eluting the product with 10% ethyl acetate/petroleum ether giving 5 (30.1 g).

MS Da/e=368 (M+Na).

(±)-2,3-Dihydro-3-ethyl-3-butyl-5-H-7-chloro-8-methoxy-1,5-benzothiazepine-4-one (6). To a suspension of 5 (72.0 g) in tetradecane (900 ml) was added toluene sulfonic acid (3.2 g). The mixture was heated to reflux temperature and allowed to reflux for 15 min collecting 4 ml $H_2O$ in a Dean-Stark trap. The solution was allowed to cool and transferred to a 1 liter erlenmeyer flask that was allowed to sit for 18 h at 4° C. The tetradecane was decanted leaving solids that were recrystallized from methanol/water. The mother liquors and the tetradecane solution were applied to a silica gel column and the remaining product eluted with 20% ethyl acetate/petroleum ether. The columned material was combined with the recrystallized material giving 6 (52.6 g).

MS Da/e=350 (M+Na).

Calcd for $C_{16}H_{22}NSO_2Cl$: C, 58.61; H, 6.76; N, 4.27; S, 9.78. Found: C, 58.70; H, 6.82; N, 4.23; S, 9.82.

(3R)-2,3-Dihydro-3-ethyl-3-butyl-5-H-7-chloro-8-methoxy-1,5-benzothiazepine-4-one (7). The racemic 6 (50 g) was resolved on a CHIRALPAK AD™ 10×50 cm column eluting with 100% methanol at 25° C. The s isomer eluted first, and the r isomer eluted second. After concentrating down the second peak, isolated 7 (23.28 g, 99% ee).

$^1$H NMR ($CDCl_3$) d 7.82 (s, 1H), 7.03, (s, 1H), 6.99 (s, 1H), 3.88 (s, 3H), 2.95 (s, 2H), 1.85–1.45 (m, 4H), 1.25 (m, 4H), 0.86 (m, 6H).

(3R)-2,3-Dihydro-3-ethyl-3-butyl-5-phenyl-7-chloro-8-methoxy-1,5-benzothiazepine-4-one (8). To a solution of 7 (10.0 g) in iodobenzene (75 ml) was added copper (I) iodide (0.30 g) and potassium carbonate (4.23 g). The mixture was refluxed for 5.5 h at which time it was allowed to cool to RT. The reaction mixture was loaded directly onto a silica gel column. The iodobenzene was eluted with petroleum ether, and the product was eluted with 15% ethyl acetate/petroleum ether giving 8 (10.9 g).

MS Da/e=404 (M+1), 426 (M+Na).

Calcd for $C_{22}H_{26}NSO_2Cl$: C, 65.41; H, 6.49; N, 3.47; S, 7.94. Found: C, 65.15; H, 6.59; N, 3.34; S, 7.72.

(3S)-2,3,4,5-Tetrahydro-3-ethyl-3-butyl-5-phenyl-7-chloro-8-methoxy-1,5-benzothiazepine-1,1-dioxide (9). To a 1 M solution of lithium aluminum hydride in ethyl ether (91.5 ml) was added dropwise at 0° C. a 7.2 M solution of sulfuric acid in THF (6.4 ml) and the mixture was stirred at 0° C. for 1 h. To the mixture at 0° C. was added 8 (10.9 g) in THF (75 ml). The reaction mixture was allowed to warm to RT and stirred for 3.5 h at RT at which point it was cooled back to 0° C. and a 30% (v/v) solution of $H_2O$ in THF was added dropwise. A 1 N solution of NaOH (15 ml) was added. The reaction mixture was filtered through a sintered glass funnel to remove the aluminum oxides. The filtrate was transferred to a separatory funnel and partitioned between water and ethyl ether. The aqueous layer was extracted three times with ether. The organic phase was dried ($Na_2SO_4$) and concentrated. The resulting oil was taken up in THF (175 ml). To the THF solution was added t-butanol (60 ml), N-methyl-morpholine-N-oxide (10.7 g) and osmium tetraoxide (2.5 wt % in t-butanol, 7.6 ml). The reaction mixture was stirred for 18 h at RT. The reaction mixture was transferred to a separatory funnel and partitioned between brine and ethyl acetate. The aqueous layer was extracted three times with ethyl acetate. The organic layer was dried, concentrated and the residue applied to a silica gel column. The product was eluted with 10% ethyl acetate/petroleum ether giving 9 (10.92 g).

m.p.=147.5° C.

MS Da/e=422 (M+1), 444 (M+Na).

Calcd for $C_{22}H_{28}NSO_3Cl$: C, 62.62; H, 6.69; N, 3.32; S, 7.60. Found: C, 62.53; H, 6.62; N, 3.32; S, 7.53.

(3S)-2,3,4,5-Tetrahydro-3-ethyl-3-butyl-5-phenyl-7-chloro-8-hydroxy-1,5-benzothiazepine-1,1-dioxide (Example 1). To a solution of 9 (10.92 g) in methylene chloride (150 ml) at 0° C. was added a 1 M solution of boron tribromide in methylene chloride (36.3 ml). The reaction mixture was allowed to slowly warm to RT and stirred for 18 h at which point it was cooled back to 0° C. and water (100 ml) was added dropwise. The mixture was transferred to a separatory funnel and extracted three times with methylene chloride. The organic extracts were dried, concentrated and the residue applied to a silica gel column. The product was eluted with 30% ethyl acetate/petroleum ether giving Example 1 (10.12 g).

M.P.=179.6–180.2° C.

MS Da/e=406 (M−1, negative ion mode).

Calcd for $C_{21}H_{26}NSO_3Cl$: C, 61.83; H, 6.42; N, 3.43; S, 7.86. Found: C, 61.76; H, 6.47; N, 3.37; S, 7.76.

Biological Assay (I) In vivo Inhibition of Bile Acid Reabsorption

Male Spraque-Dawley rats (CD, Charles River) weighing 220–260 gm were housed in individual cages and fed normal chow. The rats were dosed by oral gavage (1 ml/100 gm body weight) with test compounds as a suspension in 0.5% methylcellulose at 9:00 a.m. and 3:30 p.m. for two days. The control group received 0.5% methylcellose. Two hours after the morning dose on day two, the rats were given a trace amount (1.3 nmoles) of 23,25-$^{75}$Se-homocholic acid taurine ($^{75}$SeHCAT) in 1.0 ml saline orally. $^{75}$SeHCAT, a synthetic gamma emitting bile acid analog which is absorbed by the ileal bile acid active uptake system similar to taurocholic acid, has been used clinically as a measure of ileal bile acid absorption. Feces were collected over the 24 hours following $^{75}$SeHCAT administration. Fecal content of $^{75}$SeHCAT was determined using a Packard Auto-Gamma 5000 Series gamma-counter. The % inhibition of bile acid reabsorption is calculated as follows:

$$1\ minus\frac{total^{75}SeHCAT - excreted^{75}SeHCAT\ of\ treated}{total^{75}SeHCAT - excreted^{75}SeHCAT\ of\ control} \times 100 =$$

% inhibition

The percent of inhibition of bile acid reabsorption in the rat using $^{75}$SeHCAT was used to determine the $ED_{30}$ (the dose required to give 30% inhibition of bile acid uptake). 2,3,4,5-Tetrahydro-3-ethyl-3-butyl-5-phenyl-7-chloro-8-hydroxy-1,5-benzothiazepine-1,1-dioxide (Example 1 of the present invention), and the corresponding bromo compound, 2,3,4,5-tetrahydro-3-ethyl-3-butyl-5-phenyl-7-bromo-8-hydroxy-1,5-benzothiazepine-1,1-dioxide, (Example A, as described in PCT/GB95/02700), were tested back-to-back in two series of experiments with 6 rats in each set (n=12 total).

| | $ED_{30}$ (mg/kg) |
|---|---|
| Example 1 | 0.048 |
| Example A | 0.17 |

(II) Percent Cholesterol Lowering in Rats

Hypercholesterolemia was induced in male Spraque-Dawley rats (CD, Charles River weighing 200–300 g) by administration of a diet enriched in cholesterol and cholic acid. The diet was prepared from Wayne Laboratory Lab Blocks ground into meal and mechanically mixed with powdered cholesterol and cholic acid to a final concentration (by weight) of 1% and 0.5%, respectively. Prior to administration of the diet, blood was collected under halothane anesthesia by cardiac puncture to determine baseline lipid levels. Serum was obtained for analysis of total cholesterol (TC), high density lipoprotein cholesterol (HDL-C), and dextran-precipitable lipoprotein-cholesterol (VLDL+LDL). The rats were divided into groups so that each group had similar baseline serum lipid levels. Five days following the initial sampling for serum lipids the rats were fed ab lib the cholesterol-cholic acid enriched diet and compound administration was begun. The compound was administered by gavage as a suspension in 0.5% methylcellulose (1 ml/100 g body weight) b.i.d. at 9:00 a.m. and 3:00 p.m. for 3 days and at 9:00 a.m. on day four. Control animals received 0.5% methylcellulose only. The rats were bleed four hours after the last dose for the determination of serum lipids. All blood collections were done after a 4-h fast. Serum TC concentrations were determined enzymatically using reagents obtained from Seragen Diagnostics (2). Serum HDL-C was determined after selective precipitation of VLDL and LDL with dextran sulfate and magnesium sulfate, with reagents from Seragen (3). HDL-C was determined in the supernatant. VLDL+LDL cholesterol was determined as the difference between total and HDL-C. The following results were obtained for Example 1 and Example A, as defined above.

|  | Dose (mg/kg) | | |
| --- | --- | --- | --- |
|  | 0.3 | 0.1 | 0.03 |
| Example 1 | 81% | 56% | 48% |
| Example A | 53% | 17% | 14% |

The results clearly demonstrate the unexpectedly improved cholesterol-lowering properties of the compounds of the present invention.

Pharmaceutical Composition Examples

In the following Examples, the active compound can be any compound of formula (I) and/or a pharmaceutically acceptable salt, solvate, or physiologically functional derivative thereof.

(I) Tablet Compositions

The following compositions A and B can be prepared by wet granulation of ingredients (a) to (c) and (a) to (d) with a solution of povidone, followed by addition of the magnesium stearate and compression.

|  | mg/tablet | mg/tablet |
| --- | --- | --- |
| Composition A | | |
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
|  | 500 | 300 |
| Composition B | | |
| (a) Active ingredient | 250 | 250 |
| (b) Lactose 150 | 150 | — |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
|  | 500 | 300 |
| Composition C | | |
| Active ingredient | 100 | |
| Lactose | 200 | |
| Starch | 50 | |
| Povidone | 5 | |
| Magnesium Stearate | 4 | |
|  | 359 | |

The following compositions D and E can be prepared by direct compression of the admixed ingredients. The lactose used in composition E is of the direct compression type.

|  | mg/tablet |
| --- | --- |
| Composition D | |
| Active ingredient | 250 |
| Magnesium Stearate | 4 |
| Pregelatinised Starch NF15 | 146 |
|  | 400 |

|  | mg/tablet |
| --- | --- |
| Composition E | |
| Active ingredient | 250 |
| Magnesium Stearate | 5 |
| Lactose | 145 |
| Avicel | 100 |
|  | 500 |
| Composition F (Controlled release composition) | |
| (a) Active ingredient | 500 |
| (b) Hydroxypropylmethylcellulose Methocel K4M Premium) | 112 |
| (c) Lactose B.P. | 53 |
| (d) Povidone B.P.C. | 28 |
| (e) Magnesium Stearate | 7 |
|  | 700 |

The composition can be prepared by wet granulation of ingredients (a) to (c) with a solution of povidone, followed by addition of the magnesium stearate and compression.

Composition G (Enteric-coated Tablet)

Enteric-coated tablets of Composition C can be prepared by coating the tablets with 25 mg tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(II) Capsule Compositions

Composition A

Capsules can be prepared by admixing the ingredients of Composition D above and filling two-part hard gelatin capsules with the resulting mixture. Composition B (infra) may be prepared in a similar manner.

|  | mg/capsule |
| --- | --- |
| Composition B | |
| (a) Active ingredient | 250 |
| (b) Lactose B.P. | 143 |
| (c) Sodium Starch Glycollate | 25 |
| (d) Magnesium Stearate | 2 |
|  | 420 |

|               | mg/capsule |
| --- | --- |
| Composition C | |
| (a) Active ingredient | 250 |
| (b) Macrogol 4000 BP | 350 |
| | 600 |

Capsules can be prepared by melting the Macrogol 4000 BP, dispersing the active ingredient in the melt and filling two-part hard gelatin capsules therewith.

|               | mg/capsule |
| --- | --- |
| Composition D | |
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

|               | mg/capsule |
| --- | --- |
| Composition E (Controlled release capsule) | |
| (a) Active ingredient | 250 |
| (b) Microcrystalline Cellulose | 125 |
| (c) Lactose BP | 125 |
| (d) Ethyl Cellulose | 13 |
| | 513 |

The controlled release capsule composition can be prepared by extruding mixed ingredients (a) to (c) using an extruder, then spheronising and drying the extrudate. The dried pellets are coated with a release controlling membrane (d) and filled into two-part, hard gelatin capsules.

|               | mg/capsule |
| --- | --- |
| Composition F (Enteric capsule) | |
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalate | 5 |
| | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

| (III) Intravenous injection composition | |
| --- | --- |
| Active ingredient | 0.200 g |
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml glass vials (Type 1) which are sealed with sterile closures and overseals.

| (IV) Intramuscular injection composition | |
| --- | --- |
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (V) Syrup composition | |
| --- | --- |
| Active ingredient | 0.25 g |
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (VI) Suppository composition | |
| --- | --- |
|  | mg/suppository |
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

| (VII) Pessary composition | |
|---|---|
| | mg/pessary |
| Active ingredient (63 lm) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| (VIII) Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

What is claimed is:

1. A compound of formula (I)

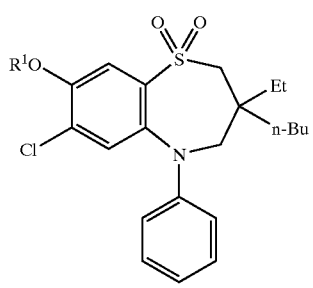

(I)

wherein
R$^1$ is H or methyl, or a salt or solvate thereof.

2. A compound selected from the group consisting of: (±)-2,3,4,5-Tetrahydro-3-ethyl-3-butyl-5-phenyl-7-chloro-8-hydroxy-1,5-benzothiazepine-1,1-dioxide; (3S)-2,3,4,5-Tetrahydro-3-ethyl-3-butyl-5-phenyl-7-chloro-8-hydroxy-1,5-benzothiazepine-1,1-dioxide; and (±)-2,3,4,5-Tetrahydro-3-ethyl-3-butyl-5-phenyl-7-chloro-8-methoxy-1,5-benzothiazepine-1,1-dioxide and salts and solvates thereof.

3. A compound selected from the group consisting of (+)-2,3,4,5-tetrahydro-3-ethyl-3-butyl-5-phenyl-7-chloro-8-hydroxy-1,5-benzothiazepine-1,1-dioxide, a salt of (±)-2,3,4,5-tetrahydro-3-ethyl-3-butyl-5-phenyl-7-chloro-8-hydroxy-1,5-benzothiazepine-1,1-dioxide, and a solvate of (±)-2,3,4,5-tetrahydro-3-ethyl-3-butyl-5-phenyl-7-chloro-8-hydroxy-1,5-benzothiazepine-1,1-dioxide.

4. A compound selected from the group consisting of (3S)-2,3,4,5-tetrahydro-3-ethyl-3-butyl-5-phenyl-7-chloro-8-hydroxy-1,5-benzothiazepine-1,1-dioxide, a salt of (3S)-2,3,4,5-tetrahydro-3-ethyl-3-butyl-5-phenyl-7-chloro-8-hydroxy-1,5-benzothiazepine-1,1-dioxide, and a solvate of (3S)-2,3,4,5-tetrahydro-3-ethyl-3-butyl-5-phenyl-7-chloro-8-hydroxy-1,5-benzothiazepine-1,1-dioxide.

5. A process for the manufacture of a compound according to claim 1, wherein R$^1$ is hydrogen, which comprises:
dealkylation of a compound of formula (II)

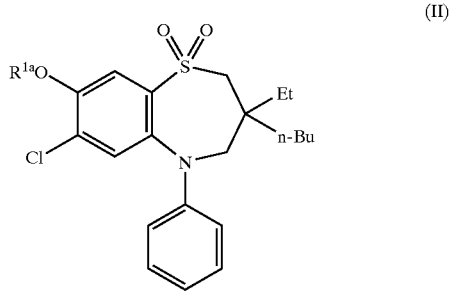

(II)

wherein R$^{1a}$ is an alkyl moiety.

6. A process for the manufacture of a compound according to claim 1, wherein R$^1$ is methyl, which comprises oxidising a compound of formula (III)

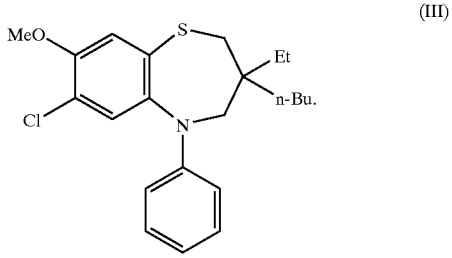

(III)

7. A pharmaceutical composition comprising a compound according to claim 1.

8. The pharmaceutical composition according to claim 7, further comprising an acceptable carrier.

9. The pharmaceutical composition according to claim 7, further comprising a physiologically active agent selected from the group consisting of bile acid sequestering agents, fibric acid derivatives, and HMG-CoA reductase inhibitors.

10. A method of prophylaxis or treating a hyperlipidemic condition in a mammal comprising administration of a therapeutically effective amount of a compound according to claim 1.

11. A method of treating atherosclerosis comprising administering a therapeutically effective amount of a compound according to claim 1.

12. A method of inhibiting the absorption of bile acids from the intestine of a mammal comprising administering an effective bile acid inhibiting amount of a compound according to claim 1.

13. A method of reducing the blood plasma or serum concentrations of LDL cholesterol in a mammal comprising administering a therapeutically effective amount of a compound according to claim 1.

* * * * *